(12) United States Patent
Dunbar et al.

(10) Patent No.: US 10,603,208 B2
(45) Date of Patent: Mar. 31, 2020

(54) MODULAR STIMULUS APPLICATOR SYSTEM AND METHOD

(75) Inventors: Peter J. Dunbar, Mercer Island, WA (US); Charles Chabal, Bellevue, WA (US)

(73) Assignee: CAREWAVE MEDICAL, INC., Seattle, WA (US)

( * ) Notice: Subject to any disclaimer, the term of this patent is extended or adjusted under 35 U.S.C. 154(b) by 124 days.

(21) Appl. No.: 13/981,081

(22) PCT Filed: Jan. 23, 2012

(86) PCT No.: PCT/US2012/022252
§ 371 (c)(1),
(2), (4) Date: Apr. 1, 2014

(87) PCT Pub. No.: WO2012/100258
PCT Pub. Date: Jul. 26, 2012

(65) Prior Publication Data
US 2014/0207219 A1 Jul. 24, 2014

Related U.S. Application Data

(60) Provisional application No. 61/435,221, filed on Jan. 21, 2011.

(51) Int. Cl.
*A61F 7/00* (2006.01)
*A61N 1/04* (2006.01)
(Continued)

(52) U.S. Cl.
CPC ............... *A61F 7/007* (2013.01); *A61H 1/00* (2013.01); *A61N 1/0408* (2013.01);
(Continued)

(58) Field of Classification Search
CPC ....................................................... A61F 7/007
See application file for complete search history.

(56) References Cited

U.S. PATENT DOCUMENTS

| 1,377,158 A | 5/1921 | Radisson et al. |
| 3,857,397 A | 12/1974 | Brosseau |

(Continued)

FOREIGN PATENT DOCUMENTS

| KR | 100915320 | 9/2009 |
| KR | 100915320 B1 | 9/2009 |

(Continued)

OTHER PUBLICATIONS

International Search Report and Written Opinion issued in PCT/US2012/022252 and dated Aug. 22, 2012 (15 pages).
(Continued)

*Primary Examiner* — Luther Behringer
(74) *Attorney, Agent, or Firm* — Perkins Coie LLP

(57) ABSTRACT

A modular stimulus applicator system and method are disclosed. The system includes a plurality of wirelessly controlled stimulus pods, anchored to a patient's body, and configured to deliver stimulus to the patient's body. The stimulus can be heat, vibration, or electrical stimulus, or any combination thereof. The stimulus pods are controlled by a control station that can include a user-interface through which the patient can control application of the stimulus.

6 Claims, 18 Drawing Sheets

(51) Int. Cl.
*A61N 1/36* (2006.01)
*A61H 1/00* (2006.01)
A61N 1/32 (2006.01)
A61H 23/02 (2006.01)

(52) U.S. Cl.
CPC ......... *A61N 1/0428* (2013.01); *A61N 1/0456* (2013.01); *A61N 1/36021* (2013.01); *A61F 2007/0078* (2013.01); *A61F 2007/0086* (2013.01); *A61F 2007/0095* (2013.01); *A61H 23/02* (2013.01); *A61H 2201/0176* (2013.01); *A61H 2201/0207* (2013.01); *A61H 2201/10* (2013.01); *A61H 2201/165* (2013.01); *A61H 2201/1614* (2013.01); *A61H 2201/1623* (2013.01); *A61H 2201/5007* (2013.01); *A61H 2201/5028* (2013.01); *A61H 2201/5046* (2013.01); *A61H 2201/5082* (2013.01); *A61H 2201/5092* (2013.01); *A61H 2201/5097* (2013.01); *A61H 2205/062* (2013.01); *A61H 2205/081* (2013.01); *A61H 2230/505* (2013.01); *A61N 1/044* (2013.01); *A61N 1/0476* (2013.01); *A61N 1/322* (2013.01)

(56) References Cited

U.S. PATENT DOCUMENTS

| | | |
|---|---|---|
| 4,107,509 A | 8/1978 | Scher et al. |
| 4,201,218 A | 5/1980 | Feldman et al. |
| 4,245,149 A | 1/1981 | Fairlie |
| 4,279,255 A | 7/1981 | Hoffman |
| 4,303,074 A | 12/1981 | Bender |
| 4,310,745 A | 1/1982 | Bender |
| 4,348,584 A | 9/1982 | Gale et al. |
| 4,396,011 A | 8/1983 | Mack et al. |
| 4,398,535 A | 8/1983 | Guibert |
| 4,518,851 A | 5/1985 | Oppitz |
| 4,575,097 A | 3/1986 | Brannigan et al. |
| 4,736,088 A | 4/1988 | Bart |
| 4,930,317 A | 6/1990 | Klein |
| 5,097,828 A | 3/1992 | Deutsch |
| 5,138,138 A | 8/1992 | Theilacker et al. |
| 5,336,255 A | 8/1994 | Kanare et al. |
| 5,423,874 A | 6/1995 | D'Alerta |
| 5,447,530 A | 9/1995 | Guibert et al. |
| 5,451,747 A | 9/1995 | Sullivan et al. |
| 5,580,350 A | 12/1996 | Guibert et al. |
| 5,601,618 A | 2/1997 | James |
| 5,658,583 A | 8/1997 | Zhang et al. |
| 5,735,889 A | 4/1998 | Burkett et al. |
| 5,741,318 A | 4/1998 | Ouellette et al. |
| 5,817,145 A | 10/1998 | Augustine et al. |
| 5,837,005 A | 11/1998 | Viltro et al. |
| 5,860,945 A | 1/1999 | Cramer et al. |
| 5,891,189 A | 4/1999 | Payne, Jr. |
| 5,893,991 A | 4/1999 | Newell |
| 5,906,637 A | 5/1999 | Davis et al. |
| 5,925,072 A | 7/1999 | Cramer et al. |
| 5,947,914 A | 9/1999 | Augustine |
| 5,964,721 A | 10/1999 | Augustine |
| 5,964,723 A | 10/1999 | Augustine |
| 5,984,995 A | 11/1999 | White |
| 5,986,163 A | 11/1999 | Augustine |
| 6,010,527 A | 1/2000 | Augustine et al. |
| 6,013,097 A | 1/2000 | Augustine et al. |
| 6,045,518 A | 4/2000 | Augustine |
| 6,066,164 A | 5/2000 | Macher et al. |
| 6,071,254 A | 6/2000 | Augustine |
| 6,095,992 A | 8/2000 | Augustine |
| 6,096,067 A | 8/2000 | Cramer et al. |
| 6,110,197 A | 8/2000 | Augustine et al. |
| 6,113,561 A | 9/2000 | Augustine |
| 6,146,732 A | 11/2000 | Davis et al. |
| 6,213,966 B1 | 4/2001 | Augustine |
| 6,217,535 B1 | 4/2001 | Augustine |
| 6,235,049 B1 | 5/2001 | Nazerian |
| 6,241,697 B1 | 6/2001 | Augustine |
| 6,248,084 B1 | 6/2001 | Augustine et al. |
| 6,264,622 B1 | 7/2001 | Augustine |
| 6,267,740 B1 | 7/2001 | Augustine et al. |
| 6,293,917 B1 | 9/2001 | Augustine et al. |
| 6,353,211 B1 | 3/2002 | Chen |
| 6,406,448 B1 | 6/2002 | Augustine |
| 6,407,307 B1 | 6/2002 | Augustine |
| 6,419,651 B1 | 7/2002 | Augustine |
| 6,423,018 B1 | 7/2002 | Augustine |
| 6,465,709 B1 | 10/2002 | Sun et al. |
| 6,468,295 B2 | 10/2002 | Augustine et al. |
| 6,485,506 B2 | 11/2002 | Augustine |
| 6,567,696 B2 | 5/2003 | Voznesensky |
| 6,572,871 B1 | 6/2003 | Church et al. |
| 6,580,012 B1 | 6/2003 | Augustine et al. |
| 6,605,012 B2 | 8/2003 | Muller |
| 6,710,313 B1 | 3/2004 | Asami et al. |
| 6,840,915 B2 | 1/2005 | Augustine |
| 6,893,453 B2 | 5/2005 | Agarwal et al. |
| 6,921,374 B2 | 7/2005 | Augustine |
| 6,925,317 B1 * | 8/2005 | Samuels ............ A61B 5/14514 600/309 |
| 7,022,093 B2 | 4/2006 | Smith et al. |
| 7,672,714 B2 * | 3/2010 | Kuo .................... A61B 5/0006 600/509 |
| 7,783,361 B2 | 8/2010 | Docherty et al. |
| 8,579,953 B1 * | 11/2013 | Dunbar et al. ................. 607/96 |
| 8,702,775 B2 | 4/2014 | Dunbar et al. |
| 2001/0037104 A1 | 11/2001 | Zhang et al. |
| 2002/0026226 A1 | 2/2002 | Ein |
| 2002/0183813 A1 | 12/2002 | Augustine et al. |
| 2003/0013998 A1 | 1/2003 | Augustine |
| 2003/0069618 A1 | 4/2003 | Smith et al. |
| 2003/0125648 A1 * | 7/2003 | Leason .............. A61H 15/0085 601/15 |
| 2004/0073258 A1 | 4/2004 | Church et al. |
| 2004/0211569 A1 | 10/2004 | Vinegar et al. |
| 2005/0256555 A1 * | 11/2005 | Fisher .................... A61F 7/007 607/96 |
| 2006/0195168 A1 * | 8/2006 | Dunbar .................. A61F 7/007 607/108 |
| 2006/0258962 A1 * | 11/2006 | Kopanic et al. ................. 601/15 |
| 2008/0091248 A1 * | 4/2008 | Libbus .............. A61N 1/36014 607/60 |
| 2008/0103567 A1 * | 5/2008 | Augustine ............... A61F 7/007 607/108 |
| 2010/0036445 A1 | 2/2010 | Sakai et al. |
| 2011/0279963 A1 * | 11/2011 | Kumar ................ A61B 5/6833 361/679.31 |

FOREIGN PATENT DOCUMENTS

| | | |
|---|---|---|
| WO | WO-8702891 A1 | 5/1987 |
| WO | 2005079295 A1 | 9/2005 |
| WO | WO-2005/079295 | 9/2005 |
| WO | 2006086513 A2 | 8/2006 |
| WO | 2008057884 A2 | 5/2008 |
| WO | WO 2008/057884 | 5/2008 |

OTHER PUBLICATIONS

International Search Report and Written Opinion, International Application No. PCT/US06/04506, dated Sep. 25, 2007, (10 pages).
Extended European Search Report for European Patent Application No. 12736967.6 dated Aug. 18, 2014, 15 pages.
Notice of Rejection for Japanese Patent Application No. 2013-550659 dated Nov. 23, 2015, 5 pages.

* cited by examiner

MODULAR STIMULUS APPLICATOR SYSTEM AND METHOD

STATEMENT OF GOVERNMENT INTEREST

The U.S. Government has a paid-up license in this invention and the right in limited circumstances to require the patent owner to license others on reasonable terms as provided for by the terms of grants 1R43CA099305-01A2, 2R44CA099305-02 and 2R44CA099305-03 awarded by the National Institutes of Health.

TECHNICAL FIELD

The following disclosure relates generally to stimulus-based therapeutic devices, systems, and methods. In particular, the disclosure relates to systems and methods for applying heat, vibration, electrical, and other stimulus to a patient's body for therapeutic purposes.

BACKGROUND

In 1965, Melzack and Wall described the physiologic mechanisms by which stimulation of large diameter non-pain sensory nerves could reduce the amount of unpleasant activity carried by pain nerves. This landmark observation published in Science was termed the "gate control theory" and offered a model to describe the interactions between various types of the sensory pathways in the peripheral and central nervous systems. The model described how non-painful sensory input such as mild electrical stimulation could reduce or gate the amount of nociceptive (painful) input that reached the central nervous system.

The gate-control theory stimulated research that lead to the creation of new medical devices such as transcutaneous electrical nerve stimulators (TENS). In brief, TENS works by electrically "blocking" pain impulses carried by peripheral nerves. Receptors to cold and heat are located just below the surface of the skin. Heat receptors are activated through a temperature range of about 36° C. to 45° C. and cold receptors by a temperature range about 1-20° C. below the normal skin temperature of 34° C. (Van Hees and Gybels, 1981). The stimuli are transmitted centrally by thin polymodal C nerve fibers. Activation of heat receptors are also affected by the rate of rise of the heat stimuli (Yarnitsky, et al., 1992). Above 45° C. warm receptor discharge decreases and nociceptive response increases producing the sensations of pain and burning (Torebjork et al., 1984).

Activation of poly-modal thermal receptors causes significant pain relief in controlled experimental conditions. Kakigi and Watanabe (1996) demonstrated that warming and cooling of the skin in human volunteers could significantly reduce the amount of reported pain and somatosensory evoked potential activity induced by the noxious stimulation of a CO2 laser. The authors offered that the effects seen could be from a central inhibitory effect produced by the thermal stimulation. Similar inhibition of pain from thermal simulation was reported in a different Human experimental pain model (Ward et al., 1996). The study authors (Kakigi and Watanabe 1996 and Ward et al., 1996) proposed that the thermal analgesia was in part from a central inhibitory effect (gating) from stimulation of small thin C nerve fibers. This contrasts with TENS which produces at least part of its analgesia through gating brought on by activation of large diameter afferent nerve fibers.

A number of recent clinical studies strongly support the use of heat as an analgesic in patients who suffer from chronic pain and offer potential mechanisms by which heat produces analgesia. Abeln et al. (2000) in a randomized controlled single-blinded study examined the effect of low level topical heat in 76 subjects who suffered from low back pain. Heat treatment was statistically more effective in relieving pain and improving the quality of sleep than that produced by placebo.

Weingand et al. (2001) examined the effects in a randomized, single blinded, controlled trial of low level topical heat in a group of over 200 subjects who suffered from low back pain and compared heat to placebo heat, an oral analgesic placebo, and ibuprofen 1200 mg/day. The authors found heat treatment more effective than placebo and superior to ibuprofen treatment in relieving pain and increasing physical function as assessed by physical examination and the Roland Morris disability scale.

A separate group (Nadler at al, 2002) found similar results in a prospective single blinded randomized controlled trial of 371 subjects who suffered from acute low back pain. The authors found that cutaneous heat treatment was more effective than oral ibuprofen 1200 mg/day, acetaminophen 4000 mg/day or oral and heat placebos in producing pain relief and improving physical function. The authors offered several hypotheses for the mechanism(s) of action which includes increased muscle relaxation, connective tissue elasticity, blood flow, and tissue healing potential provided through the low-level topical heat. Similar beneficial effects of topical heat were show shown in patients who suffered from dysmenorrhea (Akin et al., 2001), and temporomandibular joint pain TMJ (Nelson et al., 1988).

A recent study used power Doppler ultrasound to evaluate the effects of topical heat on muscle blood flow in Humans (Erasala et al., 2001). Subjects underwent 30 minutes of heating over their trapezius muscle and changes in blood flow were examined at 18 different locations over the muscle. Vascularity increased 27% (p=0.25), 77% (p=0.03) and 104% (p=0.01) with 39, 40 or 42° C. temperature of the heating pad. Importantly increases in blood flow extended approximately 3 cm deep into the muscle. The authors concluded that the increased blood flow likely contributed to the analgesic and muscle relaxation properties of the topical heat. Similar increases in deep vascular blood flow were noted using magnetic resonance thermometry in subjects treated with mild topical heat by two separate groups (Mulkern et al., 1999, and Reid et al., 1999).

Recent studies demonstrating the analgesic effectiveness of heat and provided potential mechanisms of action. The mechanisms include a reduction of pain through a central nervous system interaction mediated via thin c-fibers (Kakigi and Watanabe, 1996, Ward et al. 1996), enhancement of superficial and deeper level blood flow (Erasala et al., 2001, Mulkern et al., 1999, Reid et al., 1999), or local effects on the muscle and connective tissue (Nadler et al., 2002, Akin et al. 2001). TENS is thought to act through inhibition of nociception by increasing endogenous opioids or by a neural inhibitory interaction of nociception via large diameter fibers. It is likely that TENS and heat act partly through different mechanisms with the potential for enhanced or even synergistic interactions. TENS is widely used and endorsed by the pain management guidelines of both the AHCPR and American Geriatric Society (Gloth 2001). However a significant number of patients fail to achieve adequate relief with TENS or fail within six months of starting treatment (Fishbain et al., 1996).

DETAILED DESCRIPTION

The present disclosure is directed generally to apparatuses, devices and associated methods for applying heat to various parts of the human body using a series of modular pods. The pods can be controlled by a remote controller in the form of a computer (a desktop or a laptop computer), or a mobile device such as a mobile phone, tablet or MP3 player. The pods can releasably attach to disposable rings that adhere to the body at various locations to which the patient desires to direct heat therapy.

Several details describing thermal and electrical principles are not set forth in the following description to avoid unnecessarily obscuring embodiments of the disclosure. Moreover, although the following disclosure sets forth several embodiments of the invention, other embodiments can have different configurations, arrangements, and/or components than those described herein without departing from the spirit or scope of the present disclosure. For example, other embodiments may have additional elements, or they may lack one or more of the elements described below with reference to FIGS. 1-6.

Figure 1A:
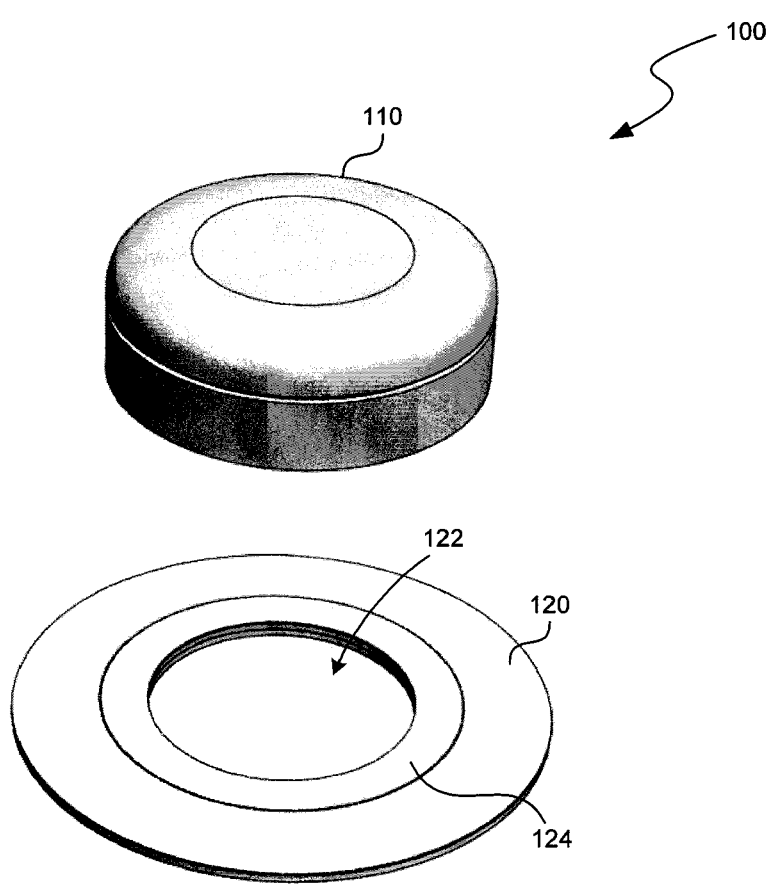
FIG. 1A is an isometric view of a heat pod and anchor according to embodiments of the present disclosure.

FIG. 1A is an illustration of a stimulus pod system 100 in accordance with several embodiments of the present disclosure. The system 100 can include a stimulus pod 110 and an anchor 120. The stimulus pod 110 can be approximately 1" in diameter, and can be equipped to deliver different stimuli to the patient's body, including heat, vibration, and electricity. In some embodiments, the pods 110 can include sensors that gather information and relay the information back to a control station. Throughout this disclosure the stimulus pods 110 are referred to interchangeably as stimulus pods 110, pods 110, or other types of pods 110 without loss of generality. The anchor 120 can have an adhesive surface that can be applied to various locations on a patient's body, an aperture 122, and an attachment ring 124 that can engage the pod 110 to hold the pod 110 onto the patient's body. Additionally or alternatively, pods 110 can be kept in place by clothing, magnets, Velcro-type applicator, elastic bands, pocket-like holders, braces, or other type of applicators capable of holding the pod against the patient's skin. The pod 110 can be a stimulus pod 110 that has a heating surface 150 that contacts the patient's body to deliver stimulus in a measured, deliberate pattern to relieve pain and discomfort in the patient's body. Several of the stimulus pods 110 can be used in concert at different places on the patient's body.

The stimulus pods 110 can also be used to deliver medicine to a patient through electrophoresis or iontophoresis. Electrophoresis is the motion of dispersed particles relative to a fluid under the influence of a spatially uniform electric field. Electrophoresis is ultimately caused by the presence of a charged interface between the particle surface and the surrounding fluid. Iontophoresis (a.k.a. Electromotive Drug Administration (EMDA)) is a technique using a small electric charge to deliver a medicine or other chemical through the skin. It is basically an injection without the needle. The technical description of this process is a non-invasive method of propelling high concentrations of a charged substance, normally a medication or bioactive agent, transdermally by repulsive electromotive force using a small electrical charge applied to an iontophoretic chamber containing a similarly charged active agent and its vehicle. One or two chambers are filled with a solution containing an active ingredient and its solvent, also called the vehicle. The positively charged chamber (anode) will repel a positively charged chemical, whereas the negatively charged chamber (cathode) will repel a negatively charged chemical into the skin.

Figure 1B:
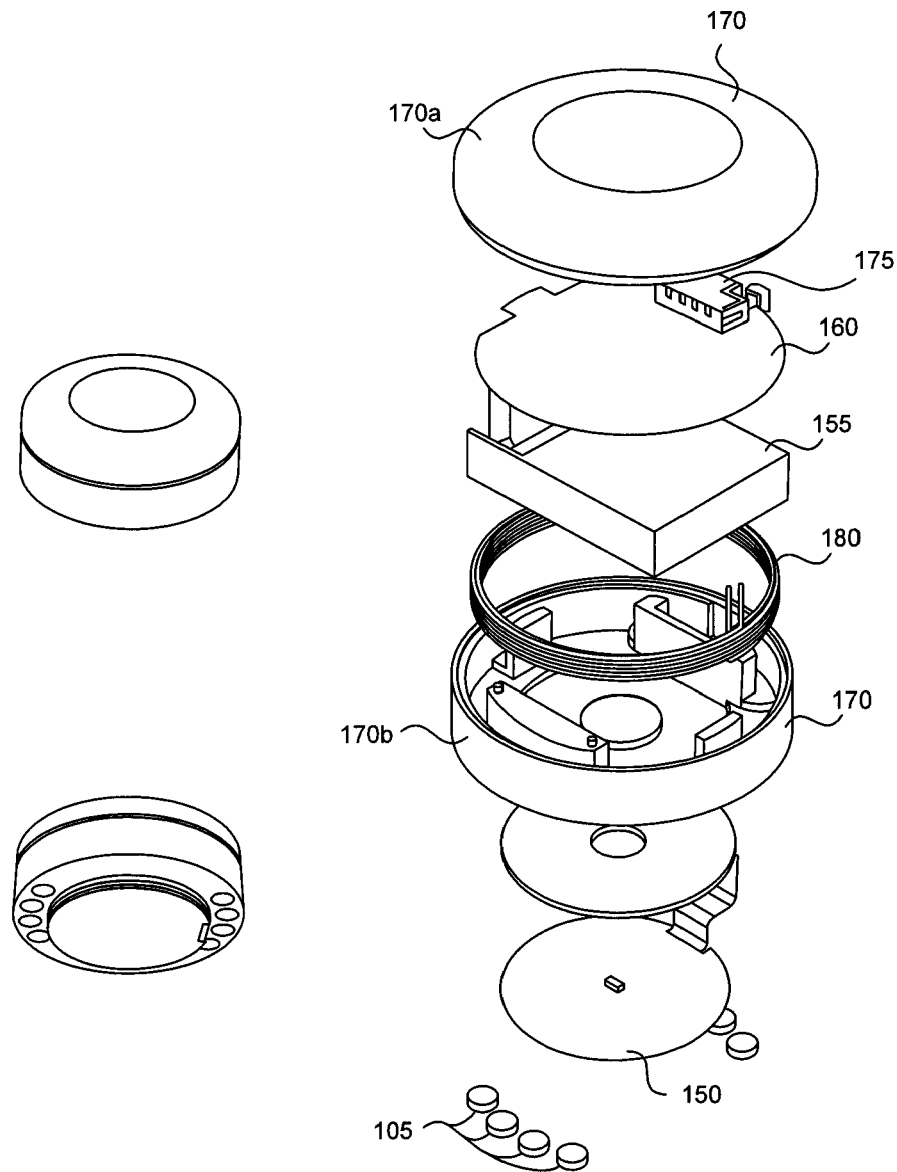
FIG. 1B is an exploded view of a heat pod according to embodiments of the present disclosure.

FIG. 1B is an exploded view of a stimulus pod 110 in accordance with several embodiments of the present disclosure. The stimulus pod 110 can include a stimulus surface 150 that contacts patient's skin to deliver heat, mild electrical stimuli, vibration, and/or other stimuli to the patient's body. The stimulus pod 110 can also include a battery 155, a circuit board 160, a charging coil 180, and several housing elements 170. The battery 155 can power the stimulus surface and the circuit board 160. The battery 155 can be a lithium polymer battery or another suitable battery type. The charging coil 180 can be configured to receive power from a power source and deliver the power to the battery 155. The stimulus pod 110 can include a wireless communication link 175 through which the stimulus pod 110 receives instructions and/or sends data to and from a control station (described in greater detail below). The housing elements 170 can include an upper cover 170a and a body 170b that enclose the internal components and provide a convenient handling surface. The stimulus pods 110 can include attachment means to attach the stimulus pod 110 to the anchor 120. For example, the stimulus pod 110 can have metal slugs 105 that can be magnetized and coupled to a metallic attachment ring 124 in the anchor 120 to hold the stimulus pod 110 to the anchor 120. The slugs 105 can also be used for stimulus delivery. In selected embodiments, the metal slugs 105 can be positioned on a top side of the stimulus pods 110 and can be used to interface with a charging station discussed in more detail below.

Figure 2:
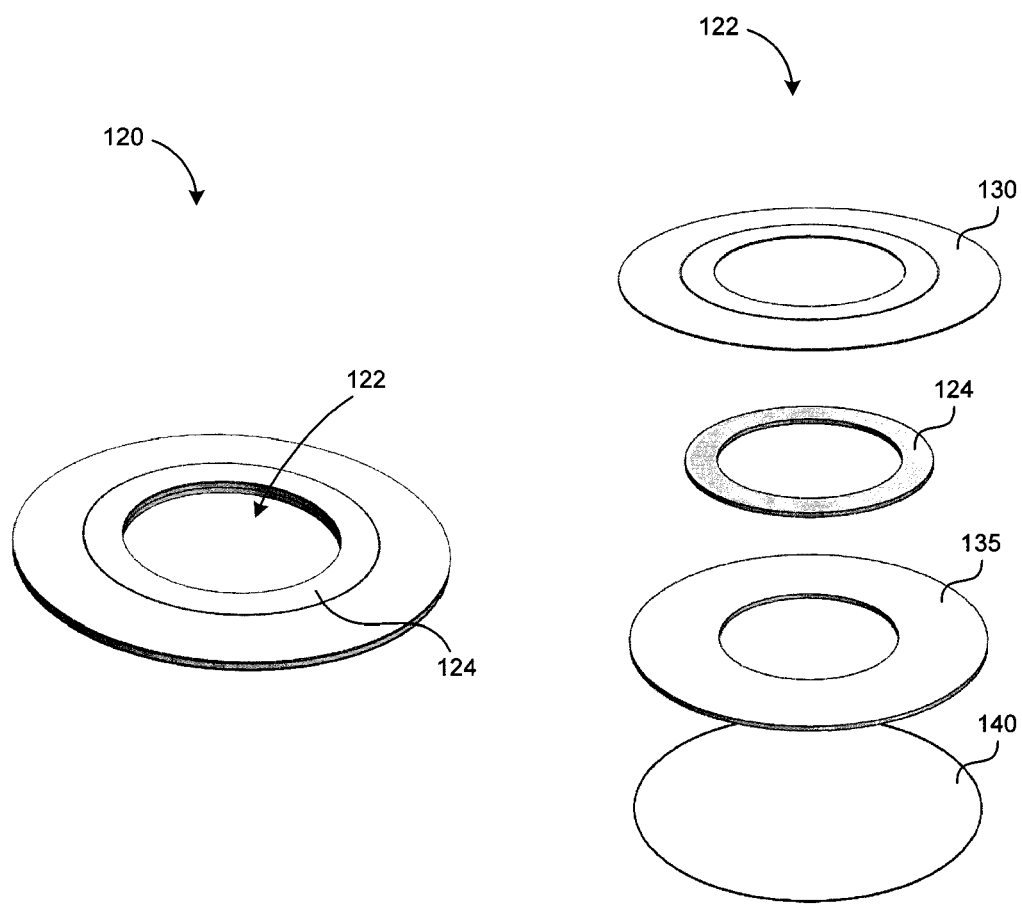
FIG. 2 is an exploded view of an anchor according to embodiments of the present disclosure.

FIG. 2 shows an anchor 120 as assembled, and in an exploded view in accordance with several embodiments of the present disclosure. The anchor 120 can include an upper surface 130, an attachment ring 124, an adhesive layer 135, and a liner 140. The liner 140 can be removed to expose the adhesive layer 135 before placing the anchor 120 on the patient's body. The upper surface 130 is exposed to the ambient conditions and accordingly can be similar to a bandage or a wound covering to provide a clean, water-resistant surface for the anchor 120. Beneath the upper surface 130, the attachment ring 124 can include a metallic ring such as a steel ring that corresponds to magnets 185 in the stimulus pod 110. The ring 124 is held to the upper surface 130 by the adhesive layer 135, which can have an adhesive on the upper side to adhere to the ring 124 and the upper surface 130, and on the lower side to adhere to the liner 140. The materials can all be rigid enough to maintain a proper shape, but flexible enough to substantially conform to the patient's body. For example, the ring 124 can be segmented or thin to permit the anchor 120 to flex to some degree. Once the anchor 120 is in its place on the body, the stimulus pod 110 can be placed into the aperture 122 in the anchor and held in contact with the patient's body to deliver heat and/or other stimulants to the patient.

Figure 3A:
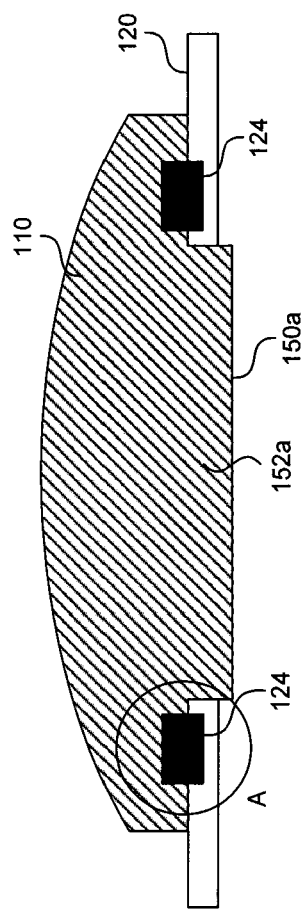
FIGS. 3A-3C illustrate various attachment means between a stimulus pod and anchor according to embodiments of the present disclosure.
Figure 3B:
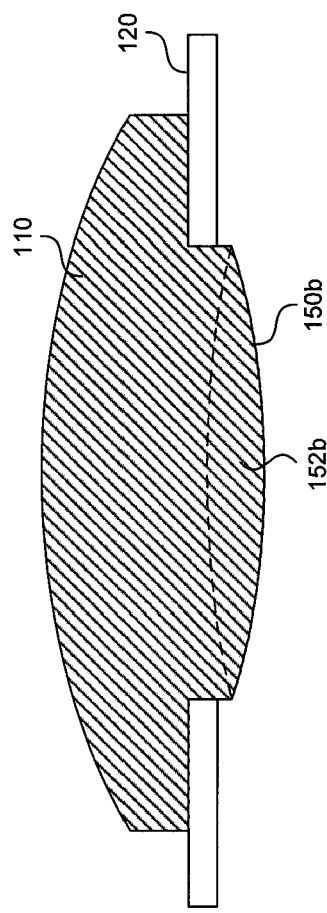
Figure 3C:
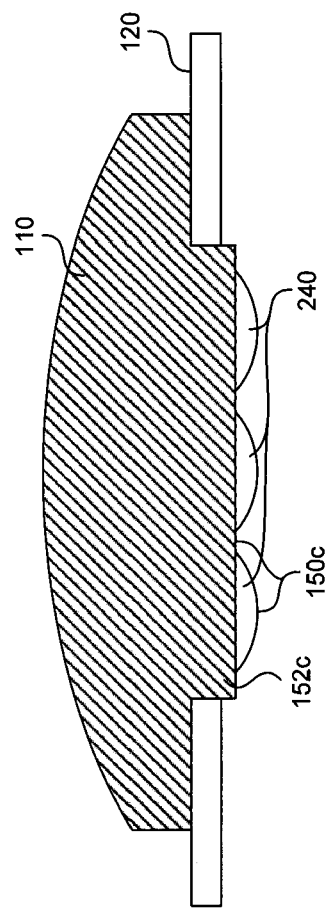

FIGS. 3A-3C illustrate several embodiments in accordance with the present disclosure including various attachment means between the anchor 120 and the stimulus pod 110. In many applications, the stimulus from the stimulus pod 110 is best delivered to the patient's body with a stimulus surface 150 directly contacting the patient's skin. The anchor can take different forms to keep the stimulus surface 150 against the patient's skin, some of which are shown using the cross-sectional views of FIGS. 3A-3C. FIG. 3A shows a stimulus pod 110 having a plug 152a that extends slightly beyond the anchor 120. The plug 152a can have a stimulus surface 150a with a flat profile. The attachment ring 124 can engage the stimulus pod 110 with sufficient force that the stimulus surface 150a presses down onto the patient's skin to ensure sufficient contact with the skin. FIG. 3B shows an alternative embodiment including a plug 152b with a stimulus surface 150b that is convex. The slope of the convex stimulus surface 152b can depend in part on the application and size of the stimulus pod 110. The convex stimulus surface 150b can have more surface area than the flat stimulus surface 150a, provided that the slope is not too extreme such that portions of the stimulus surface 150b do not contact the patient's skin. FIG. 3C illustrates yet another embodiment including a plug 152c that similarly extends beyond the anchor 120, and has a stimulus surface 150c. In this embodiment, the stimulus surface 150c has several small bumps or projections 240. The dimensions of the stimulus surface 150c and the bumps 240 can be chosen to increase the surface area of the stimulus surface 150c that contacts the patient's skin without creating void spaces or air pockets between the bumps 240 that might reduce effective heat transfer or delivery of other stimuli. In some embodiments, the projections 240 are not discrete, but are continuous and/or sinusoidal.

Figure 4:
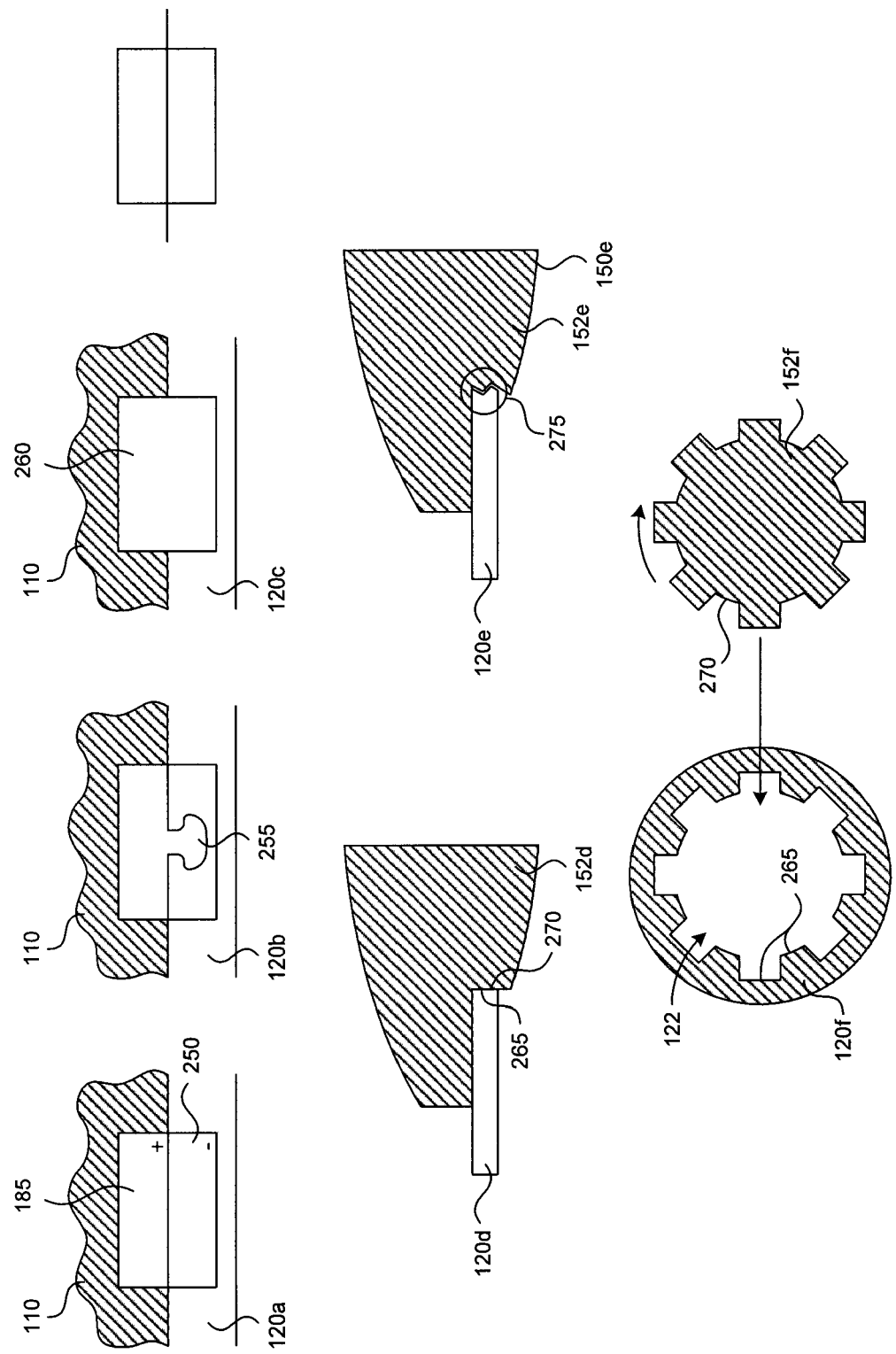
FIG. 4 shows various attachment means between a stimulus pod and anchor according to embodiments of the present disclosure.

FIG. 4 illustrates several embodiments of the present disclosure in which the attachment means between the anchor 120a and the stimulus pod 110 include various attaching mechanisms. FIG. 3A contains several magnified views of a region marked "A" which depicts the interface between the anchor 120a and the stimulus pod 110. In some embodiments, the anchor 120a contains a metallic or magnetic ring 250 that corresponds to a magnet 185 in the stimulus pod 110. The magnetic force between the ring 250 and the magnets 185 hold the stimulus pod 110 in place relative to the anchor 120a. In other embodiments, an anchor 120b can be held to the stimulus pod 110 by a mechanical fastener 255 such as a snap, or other similar mechanical attachment means. In some embodiments, the attachment mechanism can operate along the same principle as a plastic cap on a cardboard cup, such as a coffee cup and lid. Either the stimulus pod 110 or the anchor 120b can contain a resilient recession and the other can contain a matching, resilient projection that, when pressed together, mechanically hold the stimulus pod 110 in place on the anchor 120b. In still other embodiments, a hook-and-loop fastener 260 can be used. Other embodiments use the interior surface 265 of an anchor 120d and a corresponding, resilient exterior surface 270 of a plug 152d that can be pressed into the aperture 122 of the anchor 120 and snap into place. Yet another embodiment includes opposing threaded surfaces on an anchor 120e and a plug 152e such that the stimulus pod 110 can be screwed into the anchor 120 with a stimulus surface 150e protruding beyond the anchor 120e to ensure proper contact with the patient's skin. In other embodiments, an anchor 120f can include a keyed aperture 122 having an irregular interior surface 265, and a plug 152f of the stimulus pod 110 can include a correspondingly irregular external surface 270 that can be placed over the aperture 122 and rotated slightly with portions of the irregular exterior surface 270 engaging with the anchor 120f to hold the stimulus pod 110 in place.

Any of the attachment mechanisms provide a simple way for a patient to apply a stimulus pod 110 to their body. The stimulus pods 110 can be interchangeable between anchors 120, and vice versa. A patient can use a stimulus pod 110 until the battery is depleted, and then simply swap in another stimulus pod 110 with a fresh battery. The attachment means can be strong enough and the dimensions of the stimulus pod 110 can be small enough that the stimulus pod 110 can be worn under the patient's clothing easily. The placement of the anchors 120 can vary greatly according to a predetermined diagnostic pattern or personal preference. In some embodiments, the stimulus pods 110 can be placed at an area of discomfort, such as a painful lower back. Some research suggests that placing additional stimulus pods 110 at an area remote from a problem area can also provide analgesic effects. For example, a patient may use a stimulus pod 110 at the lower back—where the pain is—but they can also use a secondary stimulus pod 110 near the shoulders or on the legs. Multiple stimulus pods 110 can be used in concert to produce an aggregate affect. As different areas of the human body have different nerve densities, in certain areas two stimulus pods 110 placed near one another are perceived as a single, large stimulus pod 110. For example, the patient's back has much lower nerve density than the face, neck, or arms. Accordingly, the patient can use a pair of small stimulus pods 110 (e.g., one or two inches in diameter) at the lower back spaced about three or four inches apart and achieve the same sensory result as a larger stimulus pod covering the entire area. An unexpected benefit of this arrangement is that much less power is required to provide the stimulus in two small areas than would be required to stimulate the entire area.

Figure 5A:
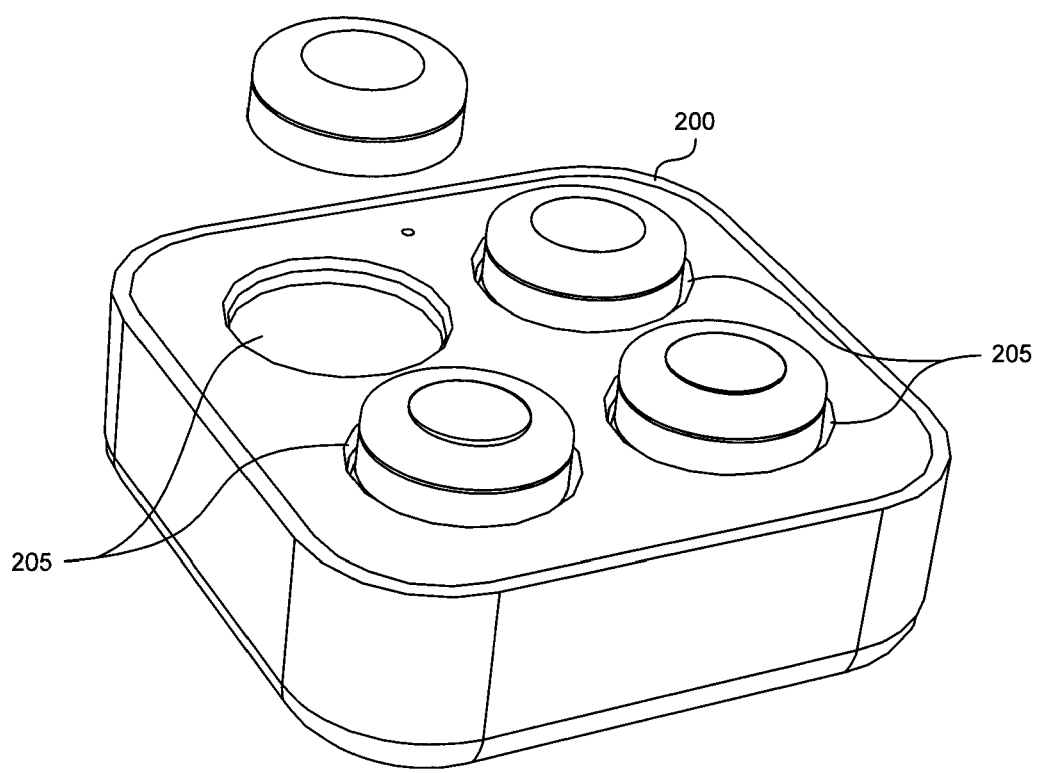
FIG. 5A is an isometric view of a non-contact charging station according to embodiments of the present disclosure.
Figure 5B:
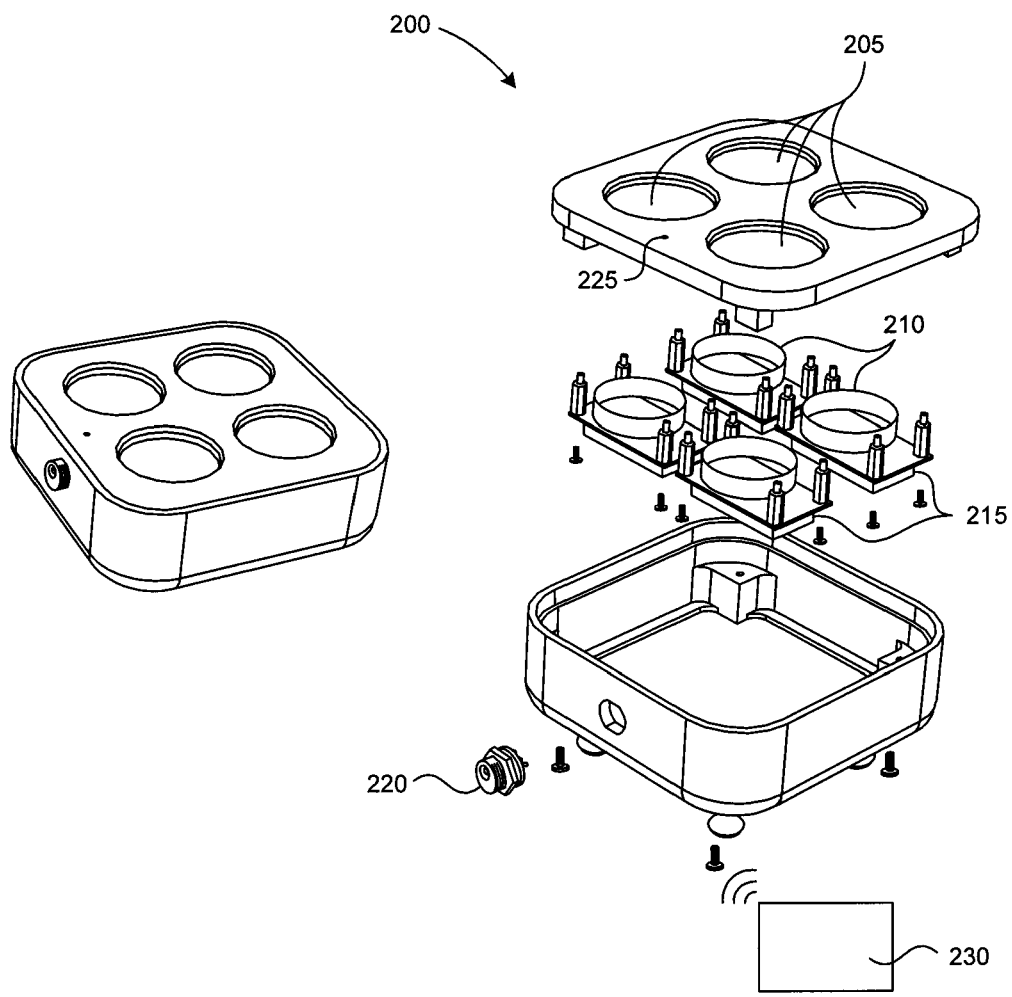
FIG. 5B is a partially exploded view of a charging and/or control station according to embodiments of the present disclosure.

FIGS. 5A and 5B illustrate a charging station 200 according to several embodiments of the present disclosure. FIG. 5A shows a charging station 200 including several sockets 205 shaped to receive a single stimulus pod 110. In the embodiment shown, the charging station 200 includes four sockets 205. Other configurations can have a different number of sockets 205. FIG. 5B is a partially exploded view of the charging station, which can include a charging coil 210 and a circuit board 215 under each socket 205. The charging station 200 can also include an electrical connector 220 that can be plugged into a standard electrical outlet or other power source to provide power to the charging station 200. The charging station 200 can detect when a stimulus pod 110 is seated in the socket 205 through a wireless signal, a proximity sensor, or because the pods 110 depress a button in the sockets 205. When the stimulus pods 110 are on the charging station 220, the corresponding circuit board 215 can instruct the charging coil 210 to transmit power to the charging coil 180 of the stimulus pod 110. In some embodiments, the stimulus pods 110 can have an asymmetric shape that matches a corresponding, negative shape in the sockets 205 to ensure proper alignment with the sockets 205. The pods 110 can include a contact point that can be used for charging the pods 110 or as control inputs for the pods 110. In another embodiment, the stimulus pods 110 can include contacts on a topside (e.g., on the upper cover 170a) through which the pods 110 can exchange electrical power and communication signals when placed on the sockets 205 with the upper cover 170a face-down. Several details of the electrical arrangement of the charging station 200, such as wires and other electrical connectors, have not been shown to avoid obscuring features of the present disclosure.

The charging station 200 can include a light 225 that can indicate that the charging station 200 is transmitting power to a stimulus pod 110. When the battery 155 of the stimulus pod 110 is fully charged, the stimulus pod 110 can notify the charging station 200 which can then cease charging the battery 155 and change the light 225 to indicate that the battery 155 is fully charged and is ready for use. When there are several stimulus pods 110 having different power levels in different sockets 205, the charging station 200 can charge the stimulus pods 110 that have less than a full charge while not powering the stimulus pods 110 that have a more full charge.

Figure 5C:
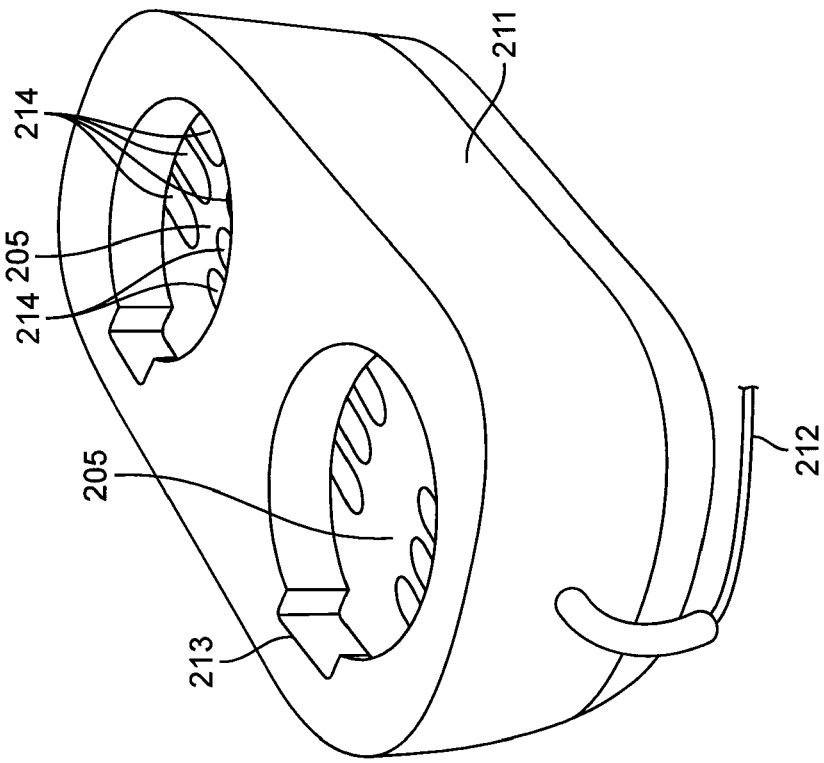
FIG. 5C is an isometric view of a contact charging station according to embodiments of the present disclosure.
Figure 5C:
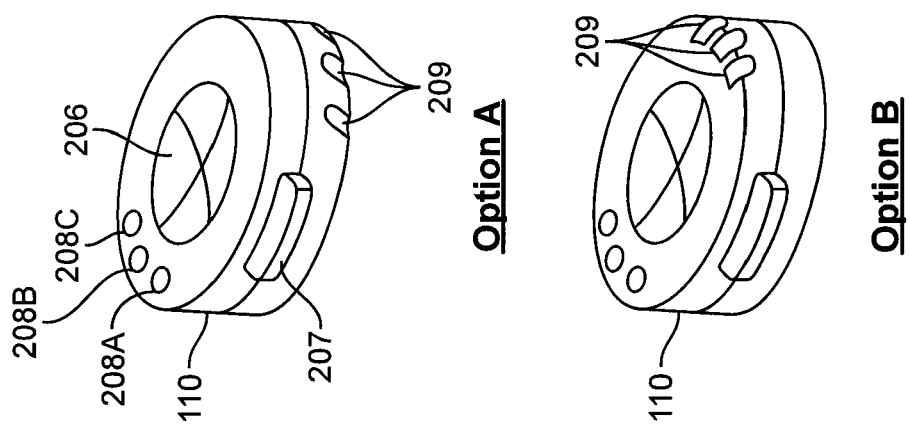

FIG. 5C shows a charging station 211 according to several embodiments of the present disclosure. The illustrated charging station 211 has two sockets 205 for receiving stimulus pods 110, but a charging station with just one or more than two sockets 205 is also possible. The charging station 211 can be plugged into a standard electrical outlet using a cord 212. Sockets 205 have socket connectors 214 that mate with pod connectors 209 when a pod is inserted into a socket. Sockets 205 can have a notch 213 to accommodate an on/off switch 207 on the stimulus pod 110. The notch 213 can also serve as a keying feature to assure proper alignment of the socket connectors with the pod connectors 209.

FIG. 5C further shows the stimulus pods 110 having the pod connectors 209 either on the lower surface of the pod (as shown in the upper view of the stimulus pod 110) or on the upper surface of the pod (as shown in the lower view of the stimulus pod 110). In some applications it may be advantageous to have the pod connectors 209 on the upper surface of the stimulus pod, because that surface is away from the patient's skin; in consequence, the connector contamination is less likely. The stimulus pod 110 can also have on/off switch 207. A simple push type on/off switch is illustrated, but many other types of switches are also possible including, for example, a slide switch, an optical switch, touch sensor, etc. In use, the on/off switch is typically activated after the contact with the patient's skin has been established, because the patient's skin provides a minimum threshold temperature below which the stimulus pod 110 will not activate, which can also be a safety mechanism preventing an accidental discharging of the stimulus pod. In addition to its power on/off function, the on/off switch 207 can be configured to control a number of heat cycles and/or temperature of the stimulus pod 110. The stimulus pod 110 can also have a heat cycle switch 206 to choose heat level like, for example, low, medium or high. The corresponding indicators 208A-C can light up in response to a particular heat cycle switch 206 setting. In the alternative, a single indicator 208 capable of changing its color can be used to indicate low, medium or high temperature. A push type heat cycle switch 206 is illustrated in FIG. 5C, but other types of switch like, for example, slide switch, multi-pole throw switch, touch sensitive switch, etc. are also possible.

In several embodiments, the stimulus pods 110 can communicate with a control station 230, shown schematically in FIG. 5B through any accepted wireless or wired protocol, including radio frequency (RF), infrared light, laser light, visible light, acoustic energy, BLUETOOTH, WIFI, or other communication systems. Additionally, the signals can be sent and received through the patient's skin. In addition to providing a communication path among the pods, sending and receiving signals through the patient's skin may be particularly well suited for determining a distance between the pods. The control station 230 can be a desktop or laptop computer, a smartphone, for example an i-Phone, or other device. The control station 230 can be included with the charging station 200, and in some cases can share components such as a power source, circuitry, etc. The control station 230 can instruct one or more stimulus pods 110 to apply heat, electric stimuli, vibration, or other stimulus or combination of stimulus in various patterns to the patient's body. In other embodiments the pods 110 include a button or series of buttons through which the pods 110 can be manually operated. The possible applications are many, and include various combinations of ramp up operations, maximum intensity operations (e.g., maximum temperature or maximum electrical current, etc.), ramp down operations, stimulus soak operations, and lockout period operations. The stimulus can be applied from different stimulus pods 110 at different levels and patterns. For example, a patient may place a stimulus pod 110 at their upper back, their lower back, and near each of their shoulders or in a different arrangement. The control station 230 can vary the stimulus application at the various zones according to a predetermined pattern. If a smartphone or other device having a screen is used as a control station, the screen may display a graphical representation of patient's body with indication as to where to locate the pods 110 in a particular application. Furthermore, the screen may display a countdown time information for all or some pods 110.

In several embodiments, the control station 230 can have information regarding the location of the stimulus pods 110 on the patient's body, and can vary the stimulus pattern accordingly. In one embodiment, the stimulus pods 110 can be built with certain body positions in mind. The stimulus pods 110 can carry body position labels to instruct the patient to apply the stimulus pods 110 according to the label. For example, in a set of four stimulus pods, two can be marked "shoulders," a third can be marked "lower back," and a fourth can be marked "upper back." In some embodiments, the anchors can communicate its location to the stimulus pod 110. The anchor 120 can include a passive identifier such as an RFID tag or other simple, passive method of communicating with the stimulus pod 110. In this embodiment, the anchor 120 can remain in place even when different stimulus pods 110 are swapped in and out of the anchor 120. The stationary anchor 120 can accurately provide location information to the control station 230 independent of which specific stimulus pod 110 occupies the anchor 120.

In other embodiments, the patient can inform the control station 230 where the stimulus pods 110 are situated, and with this information the control station 230 can apply the desired stimulus pattern to the stimulus pods 110. For example, the stimulus pods 110 can fire sequentially, and the patient can indicate the location of the stimulus on a user interface. Through the user interface, the patient can also operate the system 100 and apply treatment. In one embodiment, a control station 230 that comprises a smart phone or a computer, a graphic depiction of the patient's body can be shown and the patient can indicate to the control station 230 where the stimulus pods 110 are located. Alternatively, the patient can directly control the stimulus application through the stimulus pods 110 by moving a pointing device along the graphical depiction of their body to create a virtual stimulus-massage that the patient, or a healthcare professional, controls directly. In some cases the control station 230 can include a touch screen that the patient can touch to apply heat or other stimulus to various portions of their body (or to the body of another patient).

Figure 6:
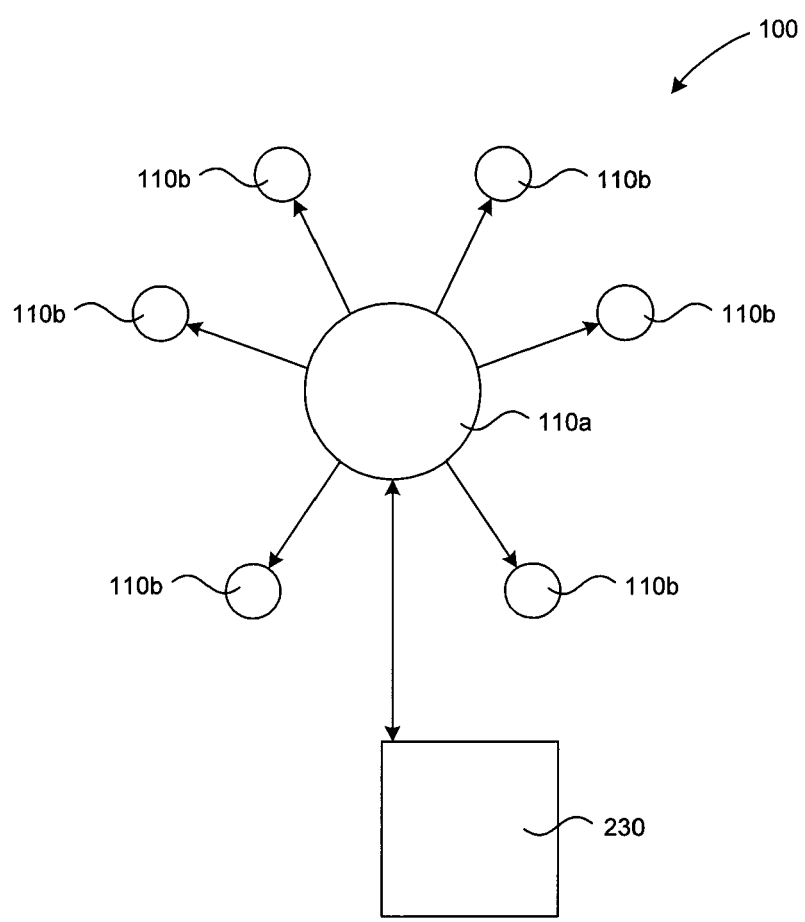
FIG. 6 is a partially schematic view of *index* stimulus pods and dummy stimulus pods, and a control station according to several embodiments of the present disclosure.

FIG. 6 depicts further embodiments of a stimulus delivery system 100 according to the present disclosure. In some embodiments, the stimulus delivery system 100 includes a control station 230, at least one index pod 110a, and several dummy pods 110b. The relationship between the index pod 110a and the dummy pods 110b can be similar to a master/drone relationship. The index pod 110a can include more sophisticated telemetry equipment than the dummy pods 110b, and can act as an intermediary between the dummy pods 110b and the control station 230. The index pod 110a may include stimulus components, such as a heating surface or vibration equipment, and can deliver stimulus just like a dummy pod 110b. Alternately, the index pod 110a can be a dedicated index pod 110a with communication equipment, but without stimulus equipment.

In some embodiments, the index pod 110a and control station 230 can discern when two or more stimulus pods 110 (e.g., dummy pods 110b or index pods 110a) are near enough to one another that they can work in aggregate. If the control station 230 knows where the stimulus pods 110 are placed on the patient's body, the control station 230, through the index pods 110a, can vary the threshold distance between stimulus pods 110a, 110b as a function of nerve density at different locations on the body. For example, if the control station 230 discerns that two or more dummy and/or index pods 110a, 110b are three inches apart and on the lower back, the control station can operate the stimulus pods 110a, 110b together to effectively cover the area between the stimulus pods 110a, 110b as well as the area directly contacting the stimulus pods 110a, 110b. By comparison, if stimulus pods 110a, 110b are three inches apart, but are placed on a more sensitive area, such as the patient's face or neck, the control station 230 can determine that the aggregate effect may not be perceived to reach the area between the stimulus pods 110a, 110b because of the greater nerve density. This information can be used when applying a treatment plan that calls for stimulus on a prescribed area. The control station can determine whether there is a stimulus pod 110 on or near the prescribed area, and if not, whether the aggregate effect from two or more stimulus pods 110 can be used to carry out the treatment plan, and can execute the plan through the pods 110.

Figure 7A:
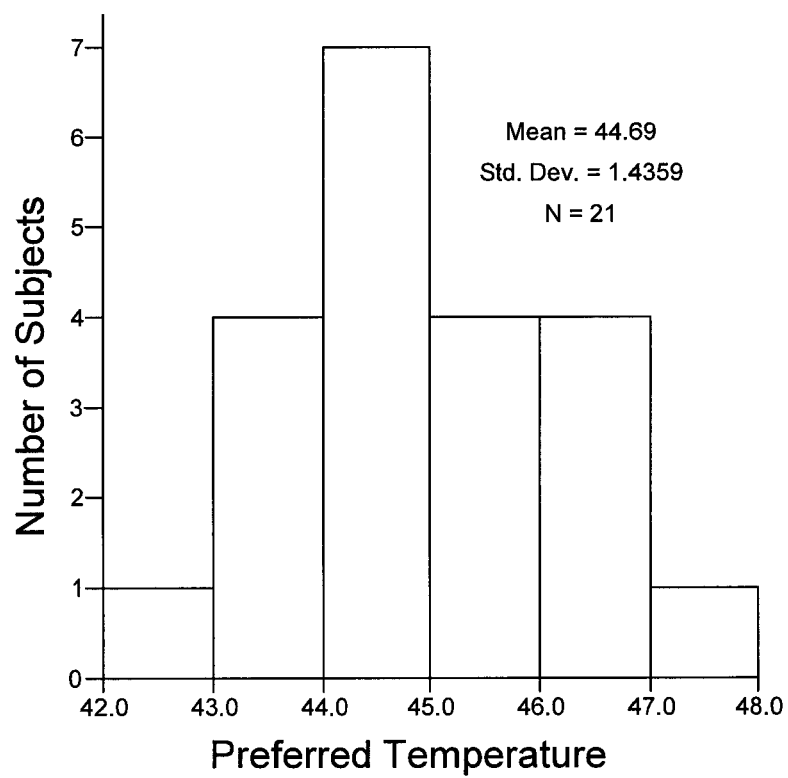
FIG. 7A is a graph of distribution of preferred pod temperature.
Figure 7B:
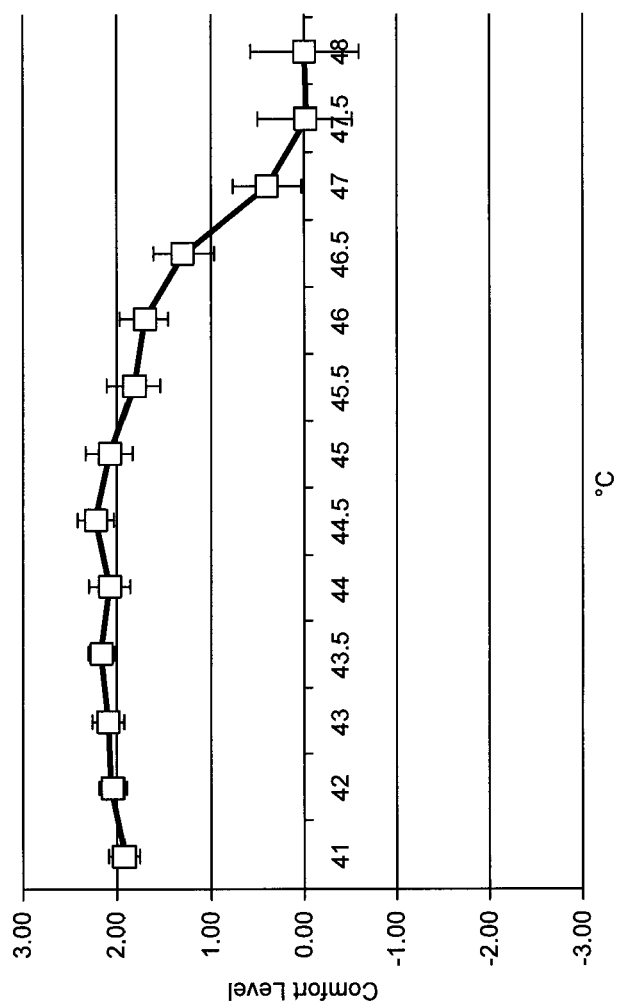
FIG. 7B is a graph of comfort values for different temperatures.
Figure 8A:
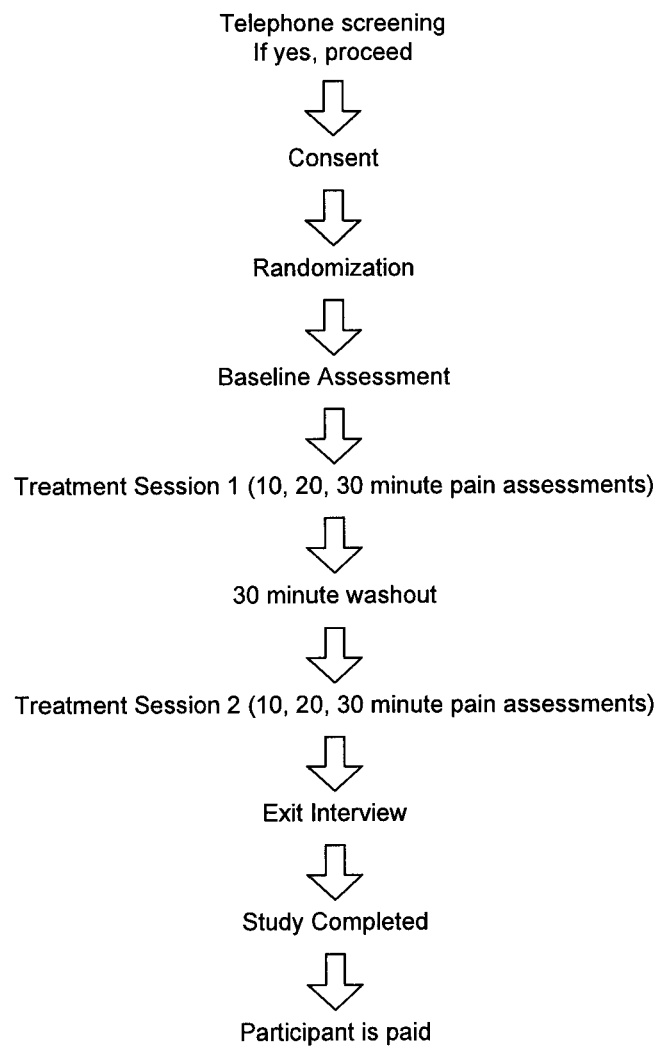
FIG. 8A is a flow diagram illustrating clinical trial procedures.
Figure 8B:
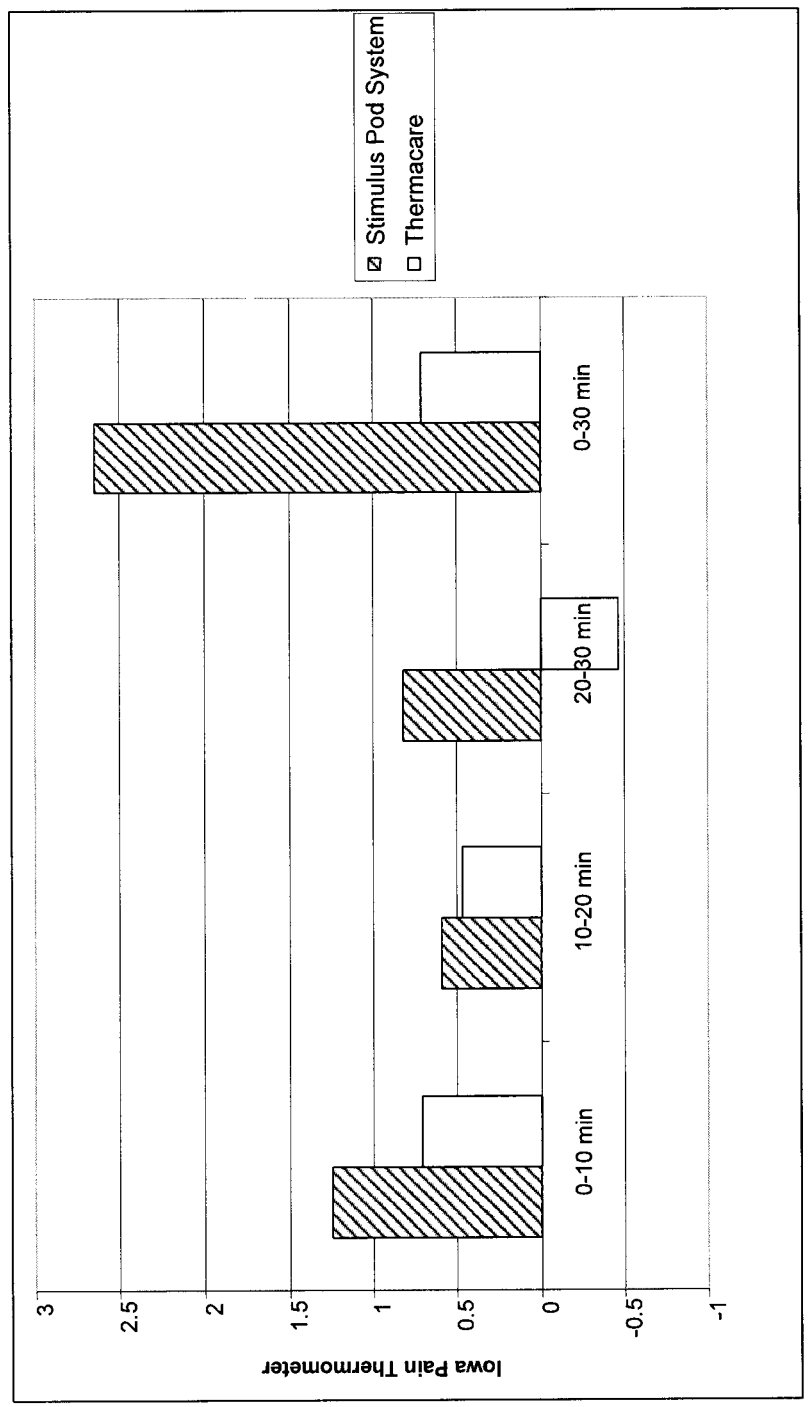
FIG. 8B is a graph comparing Iowa Pain Thermometer scales for different PMS pain treatments.
Figure 8C:
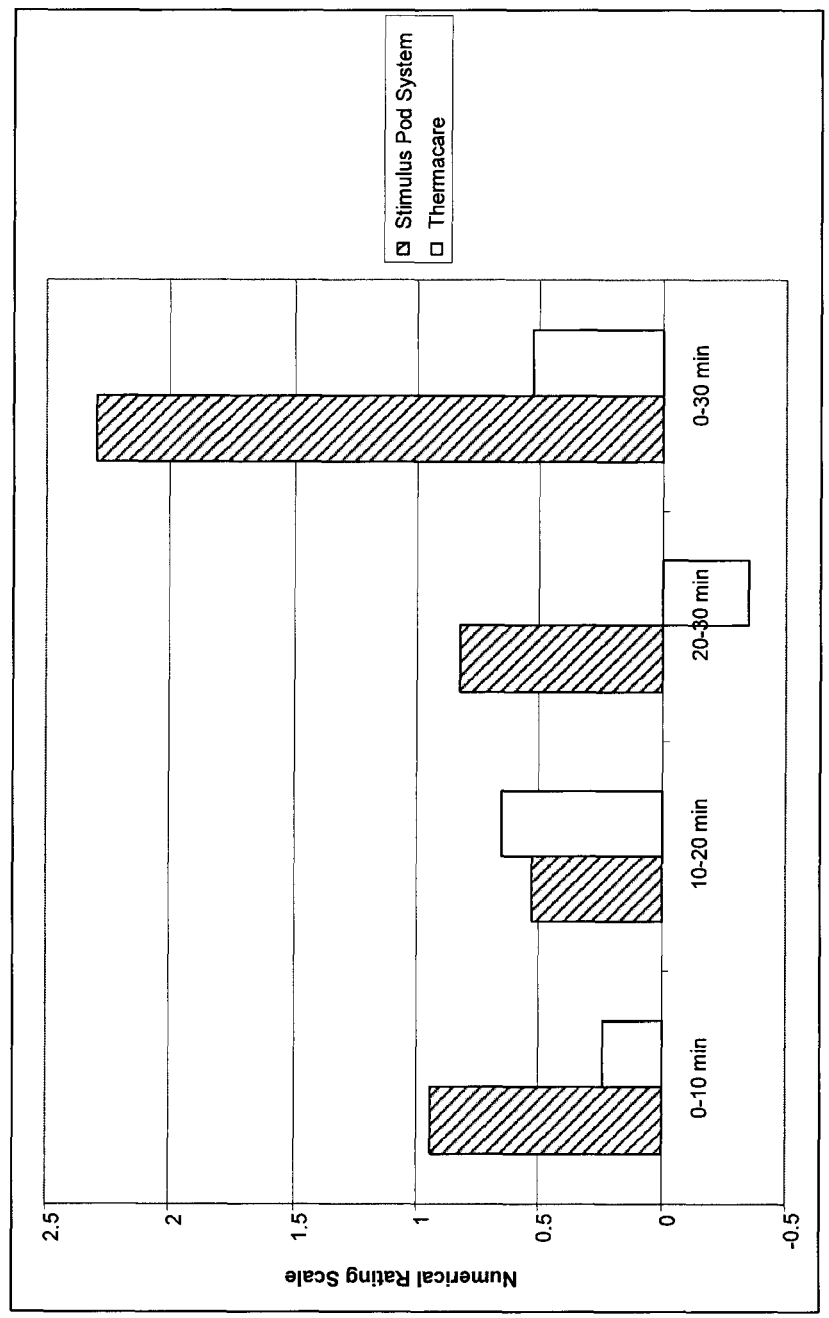
FIG. 8C is a graph comparing Numerical Rating Scales for different PMS pain treatments.
Figure 9A:
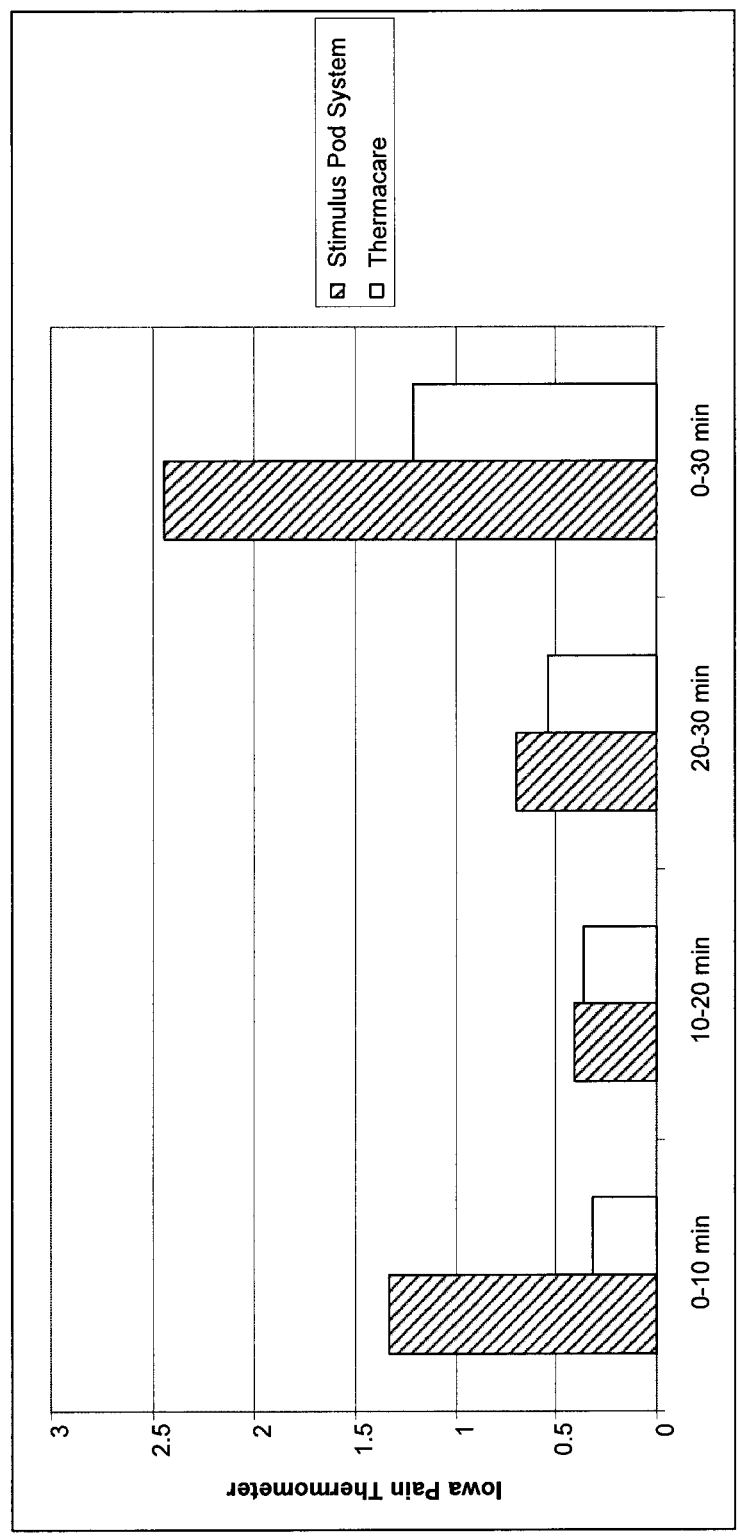
FIG. 9A is a graph comparing Iowa Pain Thermometer scales for different lower back pain treatments.
Figure 9B:
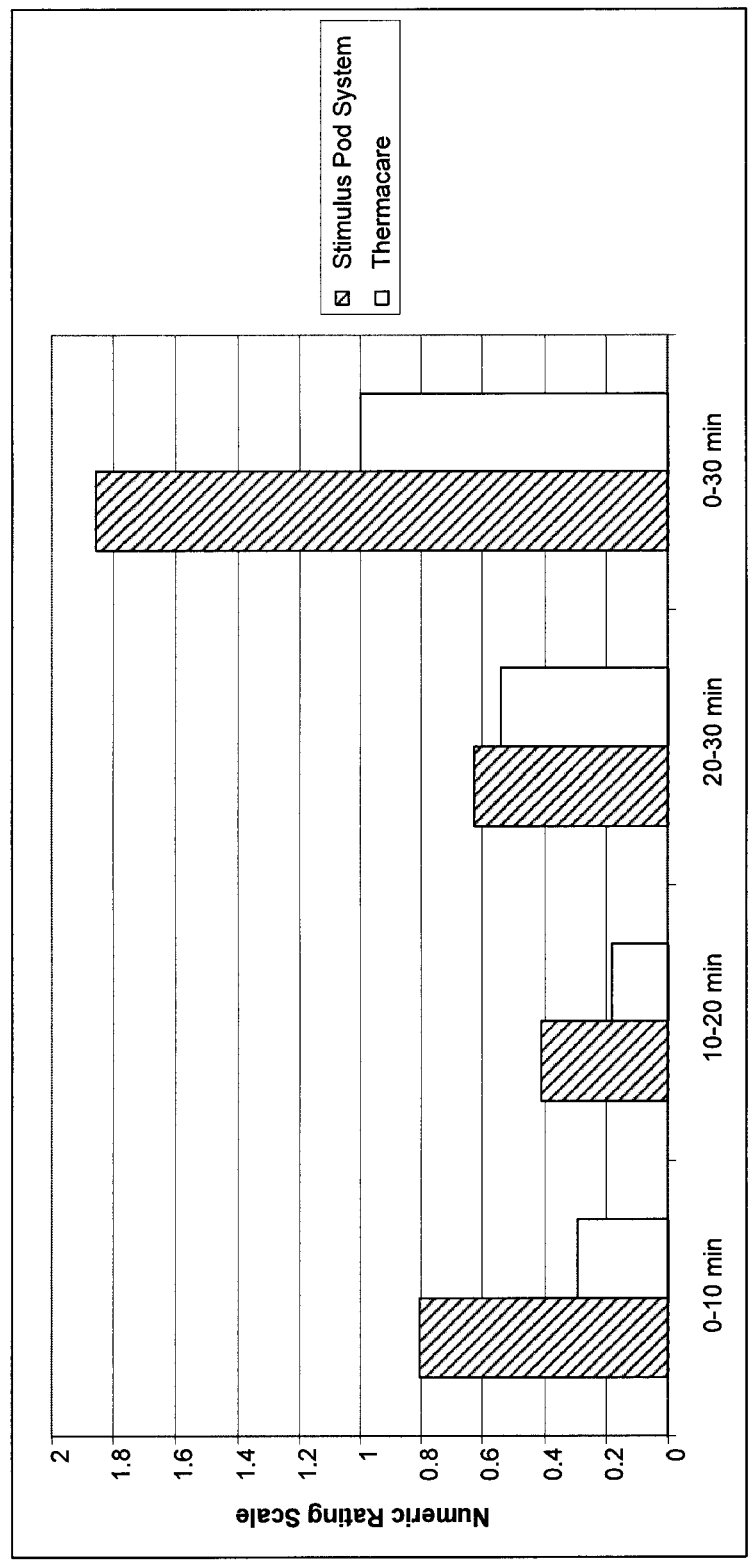
FIG. 9B is a graph comparing Numerical Rating Scales for different lower back pain treatments.

Several clinical studies were performed to evaluate effectiveness of the stimulus pod system. Details of the clinical studies and the results are provided below. FIGS. 7A-D show the results of a study that was designed to understand how to optimize heat levels, intermittency and heat distribution to produce more effective analgesia (pain relief). FIGS. 8A-C show comparison results between a ThermaCare heater and the stimulus pod system as in this invention treating the pre-menstrual syndrom. FIGS. 9A-C show comparison results between the ThermaCare heater and the stimulus pod system as in this invention when treating lower back pain.

Study of Characteristics of Thermal Analgesia in Human Subjects

A stimulus pod system for the clinical study was designed and built to optimize heat levels, intermittency and distribution. The stimulus pod system included a software controller, a set of instructions on a laptop computer and a hardware interface that connected a variety of stimulus pods to the laptop controller. A person skilled in the art would know that many types of controllers and interfaces could be used for the modular stimulus applicator system including, for example, off-shelf dedicated controllers and a software based controller on a smart phone or a tablet computer connected through a wireless or wired interfaces to the stimulus pod system. The software controller was used to control thermal variables. These variables include:

maximum temperature (° C.) of the high heat cycle (T-max);

rate of temperature climb (Δ° C./seconds) for the initial heat cycle (T1-Ramp-up);

duration of T-max (seconds) (T-max time);

rate of temperature reduction (Δ° C./seconds) to the baseline soak temperature (Ramp-down). There was no active cooling, so the Ramp-down time was a passive variable;

minimum temperature (° C.) of the low heat cycle (T-soak);

duration of T-soak (seconds) (T-soak time);

rate of temperature climb (Δ° C./seconds) for the subsequent heat cycle (T2-Ramp-up);

wave forms of both the high heat (T-max) and low heat (T-soak) cycles (a square wave form or a saw tooth pattern). The temperature difference between the peak and valley of the saw tooth heat waves was controllable;

time (in seconds) from the beginning of one ramp up period to the beginning of the next ramp up period (Heat cycle); and time (in minutes) of a number of sequential heat cycles (demand cycle).

The control laptop was connected via a USB port to a heating interface unit. This interface allowed controlling one to four stimulus pods. The pods had electrical resistance pads with embedded thermistors, which allowed for very tight control of temperature. The study initially utilized three sizes of stimulus pods: small (0.5×0.5 inches), medium (1×1 inches) and large (1.5×1.5 inches). The stimulus pods were connected to the heating interface unit with 8 ft long cables that allowed test subjects to move about the testing station.

The protocol was initially tested on 10 in-house subjects. Afterwards, a total of 23 outside subjects completed the entire initial protocol which was done in one 90 minute session. The results of the in-house testing were similar to the formal trial results. Within the group of 23 test subjects, 14 were females (61%) and 9 males (39%) with a mean age of 31 years (range 17-59, standard deviation ±9.9 years). The subjects were given explanation about the study procedure and study device. In an initial subset of subjects, each subject tried three different sizes of stimulus pods (small, medium, large) to determine what size was preferred for the subsequent phases of the study. The midsize stimulus pod was strongly preferred, and was used for the subsequent studies. In some instances, the subjects could not determine if the smallest pod was even heating. Also, there was no preference among the subjects for heating a larger area of the body by using a larger size (1.5×1.5 inches) stimulus pods.

Furthermore, a study was done to determine whether the subjects preferred a temperature above that which can be produced by a ThermaCare pad. Clinical observation indicated that many people who use heat as a therapy prefer temperatures which are in fact hot enough to cause hypertrophic changes of the underlying skin. These temperatures are most commonly obtained using electrical heating pads. Commercially available chemical heating pads, e.g., ThermaCare, can provide temperature only up to 40° C. The subsequent clinical observations indicated that this temperature limited the therapeutic effectiveness of chemical heating pads.

Once a subject's preferred temperature profile was determined, the subject was fitted with a variety of stimulus pods, and locations and the preferences were recorded. It was observed that the subjects were able to detect a difference in heat pulses of less than 1° C. As explained in more detail below, the subjects preferred a temperature that was significantly warmer (44.7° C.) than the 40° C. provided by ThermaCare.

The initial testing was done to determine the preferred temperature of the stimulus pods. The heating started at 41° C. for two minutes duration and then gradually increased in the 0.5° C. increments up to either a maximum temperature of 50° C. or until the subject felt that the pods were too hot. The initial ramp-up (T1-Ramp-up) was also varied and evaluated for the subject preference. FIG. 7A shows that the preferred heating pad temperature was 44.6° C. (range 42-48° C., standard deviation ±1.4° C.). Only a few subjects preferred a temperature greater than 46 degrees. Furthermore, as shown in FIG. 7B, subjects indicated that the perceived comfort of the heating pads gradually increased with the temperature up to approximately 45.5° C. Thereafter, the perceived comfort declined for most subjects. The comfort level can range from 3, which signifies "very comfortable," to −3, which signifies "very uncomfortable." The vertical bars on the plot symbols indicate confidence interval in all graphs.

Figure 7C:
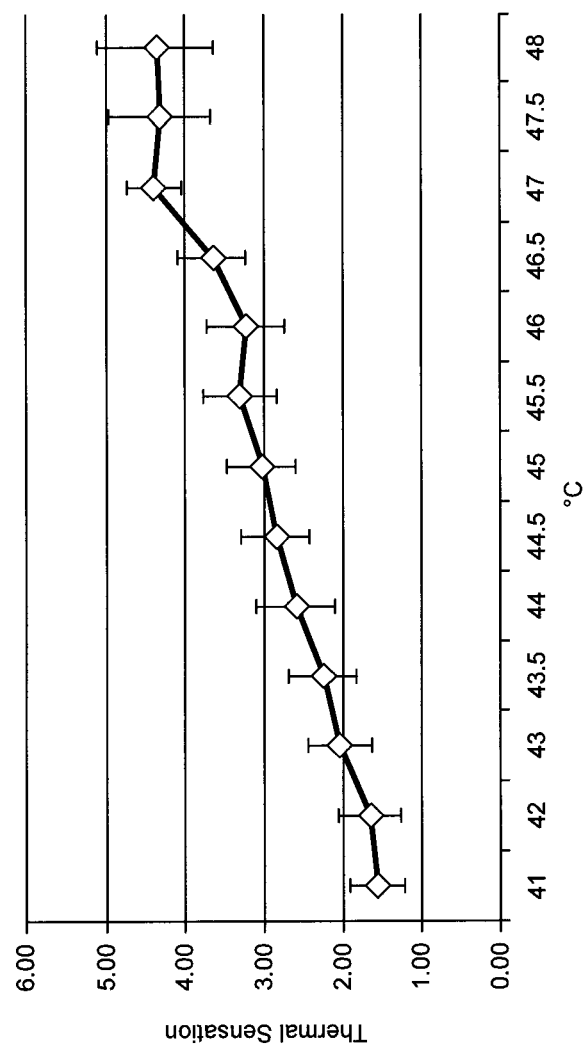
FIG. 7C is a graph of thermal sensation values for different temperatures.
Figure 7D:
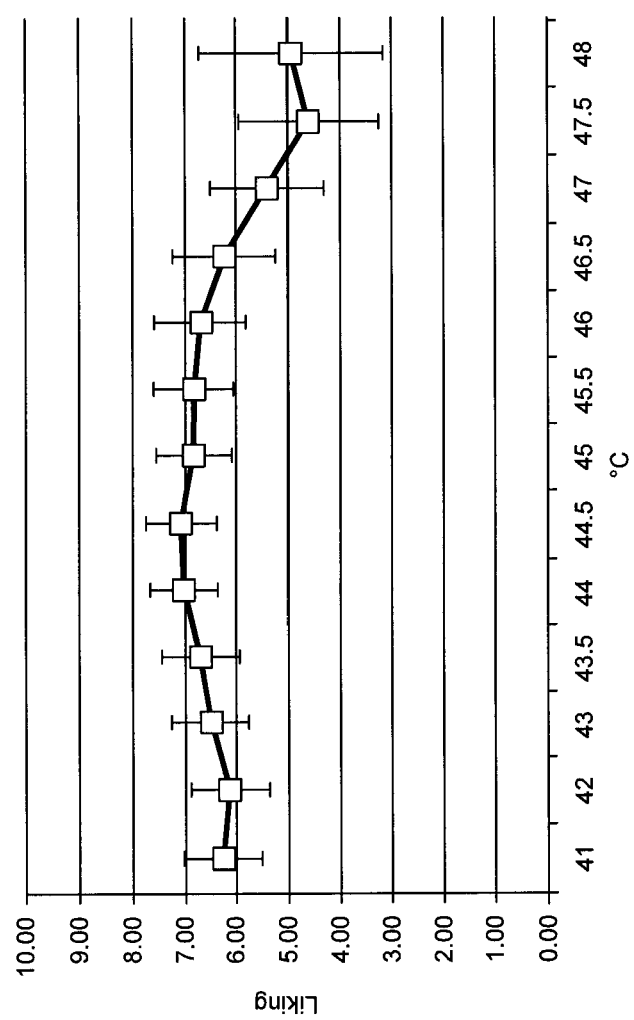
FIG. 7D is a graph of temperature "liking" values.

The temperature preferences and ratings were quantified using a thermal sensation scale that progressed from "very cold," "cold," "slightly cool," "neutral," "slightly warm," "warm," "hot," to "very hot." As shown in FIG. 7C, the subjects indicated that the pads felt increasingly warmer up to about 47° C. In the graph of FIG. 7C, the thermal sensation is scales from 0 (temperature neutral) to 6 (very hot). For the temperature above about 46° C., the temperature was rated as a "hot" or "very hot." As shown in FIG. 7D, the subjects indicated a gradual increase in "liking" of the temperature until about 46° C. The "liking" was on the scale of 0 (terrible) to 10 (wonderful). The temperature range from about 44° C. to about 46° C. was the closest to "wonderful." Outside of the 44° C. to 46° C. range, the temperature "liking" was falling away from "wonderful."

It was also observed that some subjects liked an additional pod placed on their body distant to the area that was painful. This is likely just a distraction effect, but it still increased the effectiveness of the heating pod that was placed over the body part in pain.

In summary, this study systematically evaluated properties of heat that are likely to relate to thermal analgesia. The subjects preferred temperatures that were significantly hotter than the 40° C., which can be provided by chemical heat packs such as, for example, ThermaCare. The actual or optimal temperature preferred by the subjects varied and approached a a bell shaped distribution. Initially, it was assumed that the small size heating pods (0.5×0.5 inches) or the large size heating pods (1.5×1.5 inches) would be preferred by subjects. However, the medium size pods were the most preferred. It is possible that the small pods were too small to optimally stimulate the cutaneous thermal receptive fields. In many instances when subjects were asked how large of an area was being stimulated both the medium and large pods produced a heated area that was similar in size. In most instances once the pods were removed, subjects continued to report that the skin still felt as if it was being heated. Furthermore, in several subjects with a painful area of the body not being heated e.g., neck, reported that this proximal unheated area "felt better" when a distant area e.g., low back was heated.

The above clinical study demonstrated a "dose response" in the subjects. There is also a distinct fall-off as temperatures increase above 45-46° C. The distribution is relatively tight, and it provides little margin for error with analgesic devices, such as chemical heat packs with poorly controlled or too low temperature. Furthermore, it is possible that heat pulses may provide more stimulation of the cutaneous receptors in comparison to a steady heat wave.

Study of Heat Treatment of Premenstrual Syndrome (PMS) Pain

FIGS. 8A-C illustrate the results of clinical studies of the stimulus pod system as applied for the treatment of PMS and dysmenorrhea (menstrual cramps felt during menstrual periods). PMS affects a large percentage of women—more than 50 percent of all women who have a menstrual period. About 20% to 40% of women experience symptoms that make life difficult. Approximately 5 to 15 percent of these women have severe pain that interferes with daily activities. Additionally, 2.5% to 5% experience PMS that is debilitating. Heat is a well recognized self treatment technique used to help relieve the cramps and the pains (back, abdominal and pelvic) associated with PMS. In spite of both empiric evidence and formal studies little is known about mechanisms or heat doses that are effective for PMS relief. Recent studies demonstrate that low level heat can significantly reduce PMS pain, and can even reduce the amount of pain medications used to treat PMS.

The hypothesis of this study was that a high level pulsed heat would be more effective than a low level continuous heat in relieving pain associated with PMS. The study compared analgesic effects of the stimulus pod system as in this invention with those of a commercially available ThermaCare® wrap. The stimulus pod system consisted of two heating pads that can be set to a temperature selected by the individual subject. The temperature range of the heater could be set between and including 42 to 47° C. The ThermaCare wrap is a commercial product available over the counter. The ThermaCare wrap is attached to the skin using its own elastic wrap. ThermaCare heats at a steady 40° C.

All subjects met with a research assistant (RA) prior to the start of the study. The RA explained and demonstrated the heating devices operation, their purpose and the methods of the study. The subjects were randomly assigned to one of two groups: the stimulus pod system or the ThermaCare group. All subjects completed a brief questionnaire about their pain. The study flow is illustrated in FIG. 8A.

Subjects rated their PMS pain level using Numeric Pain Scale and Iowa Pain Thermometer. Those subjects who were initially assigned to the ThermaCare had the device placed over their area of greatest pain (anterior abdomen or lower back). ThermaCare devices were allowed to warm up at least 30 minutes before being placed on the subject. Subjects rated their pain levels at baseline (time zero) and after 10, 20 and 30 minutes. After the first treatment session there was a 30 minute washout period.

Those subjects who were assigned to the stimulus pod system group were shown the study device. The RA facilitated a run-in period in which the subjects were able to gradually increase the temperature of the heating pads starting at 42° C. up to a maximum of 47° C. Once the subjects selected study temperature, the subjects wore the stimulus pod system and provided pain assessments at baseline and after 10 minutes, 20 minutes and 30 minutes. After completing the study subjects filled out an exit interview questionnaire and were paid for their participation.

FIG. 8B shows the results of the Iowa Pain Thermometer measurements for the stimulus pod system and ThermaCare. The results indicate significantly greater decrease in Iowa Pain Thermometer scores from baseline to 30 minutes when participants used the stimulus pod system device in comparison with ThermaCare use. Similar differences were found from the baseline to 10 minutes, and from the 20 to 30 minute assessment. No significant differences were found in the reduction of Iowa Pain Thermometer scores in the 10 to 20 minutes assessment.

FIG. 8C shows the results of the Numeric Rating Scale. The reduction in NRC from baseline to 30 minutes was greater when using the stimulus pod system. The subjects that used the stimulus pod system device also reported greater reduction of pain on the Numeric Rating Scale from baseline to 10 minutes, and from 20 to 30 minutes. Similarly to the Iowa Pain Thermometer scores, no significant differences were found for the two devices in the pain reduction from 10 to 20 minutes.

In conclusion, both treatments produced significant reduction in pain in the subjects suffering from PMS pain. When compared to ThermaCare, the stimulus pod system produced significantly higher pain relief. In the exit interviews, the subjects almost unanimously noted that they all preferred the warmer temperatures from the stimulus pod system than those offered by the low level heat of the ThermaCare product. Many subjects also explained that they very much liked the pulsing sensation provided by the Heater device.

Study of Heat Treatment of Low Back Pain (LBP)

FIGS. 9A-C illustrate the results of the lower back pain study. One third of all Americans suffer from back pain at some point during a given year. The estimated number of individuals in the United States that suffer from chronic pain varies from 160 million on down, but is generally cited as being close to 50 million. The lower back pain costs employers more than $60 billion a year in lost productivity. If the cost of treatment is added to that number, then the cost is estimated at about $100 billion a year. Men and women are equally affected by the back pain. The pain occurs most often to people between ages 30 and 50, due in part to the aging process, but also as a result of sedentary life styles with too little (sometimes punctuated by too much) exercise. The risk of experiencing low back pain from disc disease or spinal degeneration also increases with age. Back pain is the second most common neurological ailment in the United States—only headache is more common.

Heat has long been a mainstay treatment for low back pain. A number of recent studies demonstrated that heat reduces low back pain, improves function and may result in the use of fewer pain medications. In spite of both empiric evidence and formal studies little is known about mechanisms or dose response data for heat induced LBP relief. The hypothesis of this study was that a high level pulsed heat would be more effective than a low level continuous heat in relieving chronic low back pain.

The subjects used the stimulus pod system or ThermaCare as explained above in relation to the Study of Heat Treatment of Premenstrual Syndrome Pain. Those subjects who were randomized initially to the stimulus pod system group were shown the study device. The RA facilitated a run in period in which the subject was able to gradually increase the temperature of the heating pads starting at 42° C. up to a maximum of 47° C. Once the study temperature was selected, subjects wore the device and provided pain assessments at baseline and after 10 minutes, 20 minutes, and 30 minutes. After completing the study, all subjects filled out an exit interview questionnaire and were paid $100 for study participation.

As shown in FIG. 9A, subjects indicated significantly greater decrease in Iowa Pain Thermometer scores from the baseline to 30 minutes when the stimulus pod system was used. Similar conclusion applies to the time from the baseline to 10 minutes, and from the 20 to 30 minute assessment. No significant differences were found between the devices in reduction of the IPT scores from 10 to 20 minutes.

FIG. 9B shows that the reduction of pain rating on the Numeric Rating Scale from baseline to 30 minutes was also greater when using the stimulus pod system device. Similar to the Iowa Pain Thermometer scores, the subjects using the stimulus pod system also reported greater reduction of pain on the Numeric Rating Scale from baseline to 10 minutes, and from 20 to 30 minutes. No significant differences in the reduction of pain were found from 10 to 20 minutes.

In conclusion, both treatments (the stimulus pod system and ThermaCare) produced reduction in pain in the subjects who suffered from chronic low back pain. The stimulus pod system produced significantly higher pain relief in comparison to ThermaCare. The higher heat provided by the stimulus pod system was associated with better and more profound pain relief. In the exit interviews, subjects almost unanimously noted that they all preferred the warmer temperatures from the stimulus pod system than that offered by the low level heat of the ThermaCare product. Many subjects also stated that they very much liked the pulsing sensation provided by the Heater device.

From the foregoing, it will be appreciated that specific embodiments of the invention have been described herein for purposes of illustration, but that various modifications may be made without deviating from the spirit and scope of the various embodiments of the invention. Further, while various advantages associated with certain embodiments of the invention have been described above in the context of those embodiments, other embodiments may also exhibit such advantages, and not all embodiments need necessarily exhibit such advantages to fall within the scope of the invention. Accordingly, the invention is not limited, except as by the appended claims.

The invention claimed is:

1. A system for treating portions of a patient's body, comprising:
   a stimulus pod including a plug having an outer perimeter less than that of the stimulus pod, a contact surface configured to contact the patient's body, a battery, and a circuit board enabling control logic for the stimulus pod;
   an anchor having:
      an attachment ring including an aperture having substantially the same inner perimeter as the outer perimeter of the plug, the attachment ring configured to releasably receive the stimulus pod;
      an adhesive element configured to apply to the patient's body; and wherein the inner perimeter of the aperture is positioned to receive at least a portion of the plug of the stimulus pod such that the contact surface of the stimulus pod projects through the aperture and beyond the adhesive element to contact the patient's body; and an attachment mechanism configured to releasably attach the stimulus pod to the attachment ring with the contact surface of the stimulus pod contacting the patient's body, wherein the stimulus pod is configured to deliver stimulus to the patient's body according to the control logic.

2. The system of claim 1 wherein the stimulus pod is configured to treat the patient's body with at least one of thermal stimulus, electrical stimulus, or vibration stimulus.

3. The system of claim 1 wherein the attachment mechanism comprises at least one of a magnetic link, a resilient mechanical fastener, a hook-and-loop fastener, or a threaded fastener.

4. The system of claim 1 wherein the stimulus pod comprises a wireless communication link, the system further comprising a control station configured to communicate with the stimulus pod through a wireless communication link.

5. The system of claim 1, further comprising a charging station having a plurality of sockets shaped to receive at least one stimulus pod and to charge the battery of the stimulus pod.

6. The system of claim 1 wherein the contact surface has at least one of a flat profile, a convex profile, a series of projections, or a sinusoidal profile.

* * * * *